(12) United States Patent
Fujima (10) Patent No.: US 6,350,030 B2
(45) Date of Patent: Feb. 26, 2002

(54) FACE MASK FOR DIVER

(75) Inventor: Taro Fujima, Tokyo (JP)

(73) Assignee: Tabato Co., Ltd. (JP)

( * ) Notice: Subject to any disclaimer, the term of this patent is extended or adjusted under 35 U.S.C. 154(b) by 0 days.

(21) Appl. No.: 09/781,915

(22) Filed: Feb. 12, 2001

(30) Foreign Application Priority Data

Feb. 9, 2000 (JP) ....................................... 2000-032348

(51) Int. Cl.[7] .................................................. G02C 1/00
(52) U.S. Cl. ............................................. 351/43; 2/426
(58) Field of Search ........................... 351/43, 41, 156, 351/157; 2/426; 24/3.1, 3.3, 3.13

(56) References Cited

U.S. PATENT DOCUMENTS 5,914,766 A * 6/1999 Berke .......................... 351/43

* cited by examiner

*Primary Examiner*—Hung Xuan Dang
(74) *Attorney, Agent, or Firm*—Baker & Daniels (57) ABSTRACT

A face mask is provided with buckles, each of the buckles including a first support member and a second support member. A head strap is guided and folded back by the first support member. A spring extending in a width direction of the head strap is inserted from the front or the lateral side of the face mask into a space defined between distal ends of the first and second support members.

7 Claims, 6 Drawing Sheets

FACE MASK FOR DIVER

BACKGROUND OF THE INVENTION

This invention relates to a face mask suitable for use during diving or the like.

In the face mask used during diving or the like, it is well known to length-adjustably couple a head strap to a lens frame of the face mask by means of buckles. Each of the buckles usually comprises a first support member extending rearward from the associated lateral end of the lens frame, a second support member pivotally supported by the first support member and a spring biasing the second support member to swing so that the head strap may be held between the first and second support members. The first and second support members are placed upon each other so that the first support member may lie immediately adjacent the face mask and the second support member may lie outside the first support member. The head strap is guided and folded back by the first support member. A locking tooth formed on the second support member is adapted to be engaged with any one of plural locking teeth formed on the head strap under a biasing effect of the spring thereby to prevent the head strap from moving in its slackening direction.

The face mask of prior art uses, for example, a coil spring as the spring. In this case, the spring is set between the first and second support members so that the spring may be oriented in in-and-out direction of the face mask. The coil spring used for this purpose usually has been too small in its diameter as well as in its length to ensure that the spring can be adequately compressed and firmly inserted between the first and second support members. In addition, it has been further difficult to disassemble the spring once incorporated into the buckle for the purpose of inspection and exchange.

SUMMARY OF THE INVENTION

An object of this invention is to provide a face mask for diving provided with buckles facilitating a spring to be incorporated into or removed from each of the buckles.

In accordance with this invention, there is provided a face mask for diving comprising front lenses, a skirt extending rearward from the front lenses, a lens frame securing a front end of the skirt to a peripheral edge of the lenses, a head strap and buckles for length-adjustably coupling longitudinal opposite ends of the head strap to respective lateral ends of the lens frame.

This invention further comprises the head strap having a length direction, a width direction and a thickness direction orthogonal to the length and width directions. Each of the buckles includes a first support member and a second support member cooperating with each other to hold the head strap therebetween, the first support member extending rearward from the lateral end of the lens frame and having a guide pin extending in the width direction of the head strap so that the head strap is folded back around the guide pin, the second support member being formed separately of the lens frame and pivotally supported by the first support member around a pivot pin, the second support member having a first arm extending rearward from the pivot pin and formed with a second locking tooth adapted to be selectively engaged with one of first locking teeth formed on a section of the head strap folded back around the guide pin. Each of the buckles further includes a spring extending in the width direction of the head strap and adapted to be inserted from the front or the lateral side of the face mask into a space defined between a distal end of a second arm of the second support member extending forward from the pivot pin and a distal end of the first support member opposed to the distal end of the second support member so that the spring is compressed and elastically deformed between the distal ends to bias the second support member to swing until one of the first locking teeth comes in engagement with the second locking tooth thereby to prevent the head strap from moving in a slackening direction thereof.

In the face mask according to this invention, the buckle comprises the first support member and the second support member placed upon and pivotally supported by the first support member. The spring biasing the second support member to swing can be incorporated into the buckle merely by inserting it between the first and second support members from the front or the lateral side of the face mask. In this way, both assembly and disassembly of the buckle is facilitated and, in consequence, production, maintenance and inspection of the face mask are correspondingly facilitated. The face mask arranged so that the spring can be inserted inward radially of the face mask into the space defined between the first and second support members advantageously eliminates an anxiety that the buckles might become bulky at the mask wearer's temples and a fluid-resistance of the face mask might increase.

DETAILED DESCRIPTION OF THE PREFERRED EMBODIMENTS

Details of a face mask for diver according to this invention will be more fully understood from the description given hereunder with reference to the accompanying drawings.

Figure 1:
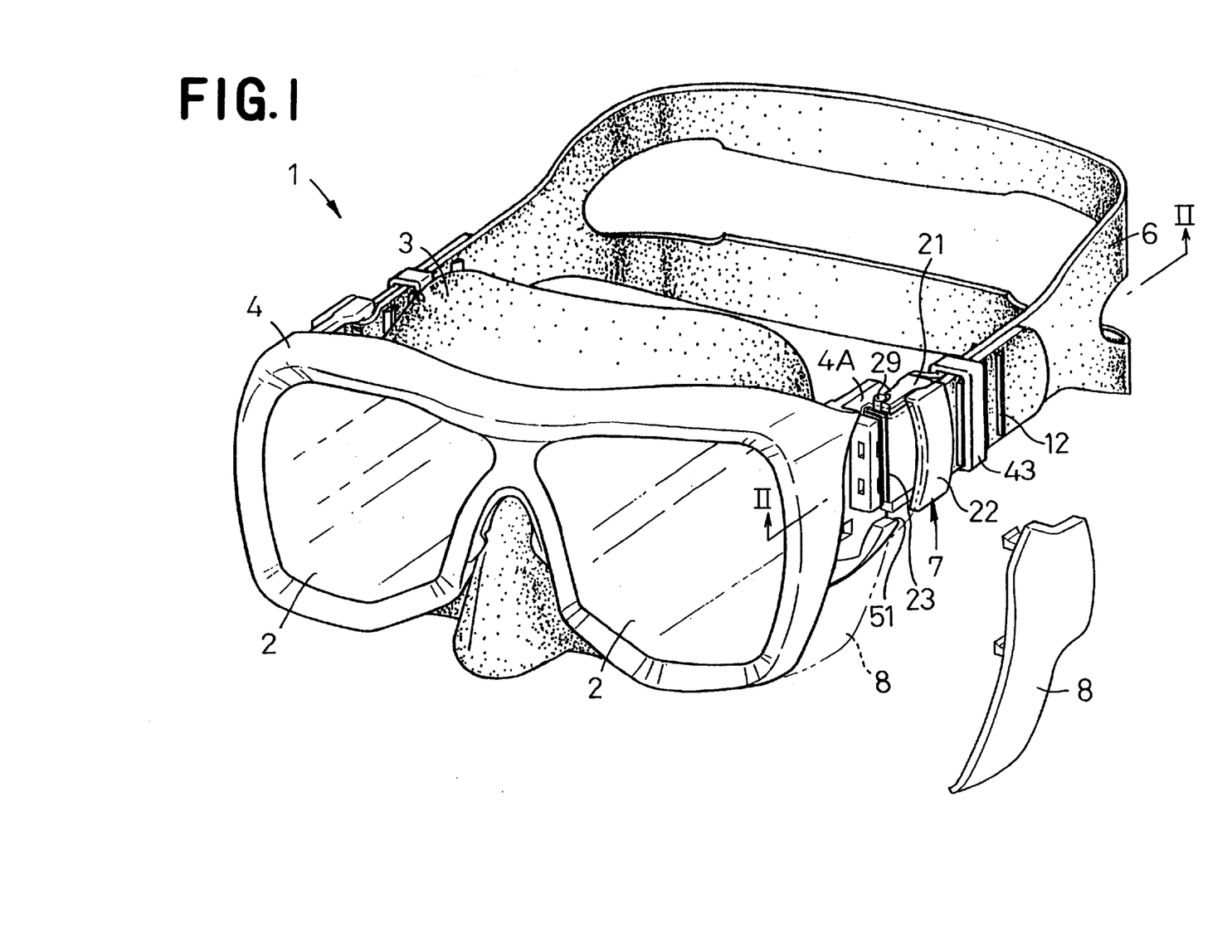
FIG. 1 is a perspective view depicting a partially exploded face mask in accordance with a principle of this invention.

A face mask 1 for diving depicted by FIG. 1 in a perspective view as partially cutaway comprises a pair of front lenses 2, a skirt 3, a lens frame 4 for securing a front end of the skirt 3 to a peripheral edge of the lenses 2, a head strap 6 put around a mask wearer's head and a pair of buckles 7 adapted to couple longitudinally opposite ends of the head strap 6 to respective lateral ends 4A of the frame 4 in a length-adjustable manner. The face mask of FIG. 1 has the frame 4 provided with detachable side covers 8 indicated by chain lines, one of which is depicted in its detached state. The head strap 6 is formed from flexible elastic material such as rubber or plastic elastomer and has a longitudinal direction extending circumferentially around the mask wearer's head, a transverse direction extending vertically as viewed in FIG. 1 and a thickness direction being orthogonal to the longitudinal and transverse directions. The longitudinally opposite ends of the head strap 6 are formed on the outer surfaces with a plurality of first locking teeth 12 extending in the vertical direction. Each of the buckles 7 comprises a first support member 21 mounted on the associated lateral end 4A of the frame 4, a second support member 22 pivotally mounted to the first support member 21 around a pivot pin 29 and a spring 23 disposed between the first and second support members 21, 22 so that the strap 6 may be held between the first and second support members 21, 22. The head strap 6 is folded back within the buckle 7 and then put together by a holder ring 43.

Figure 2:
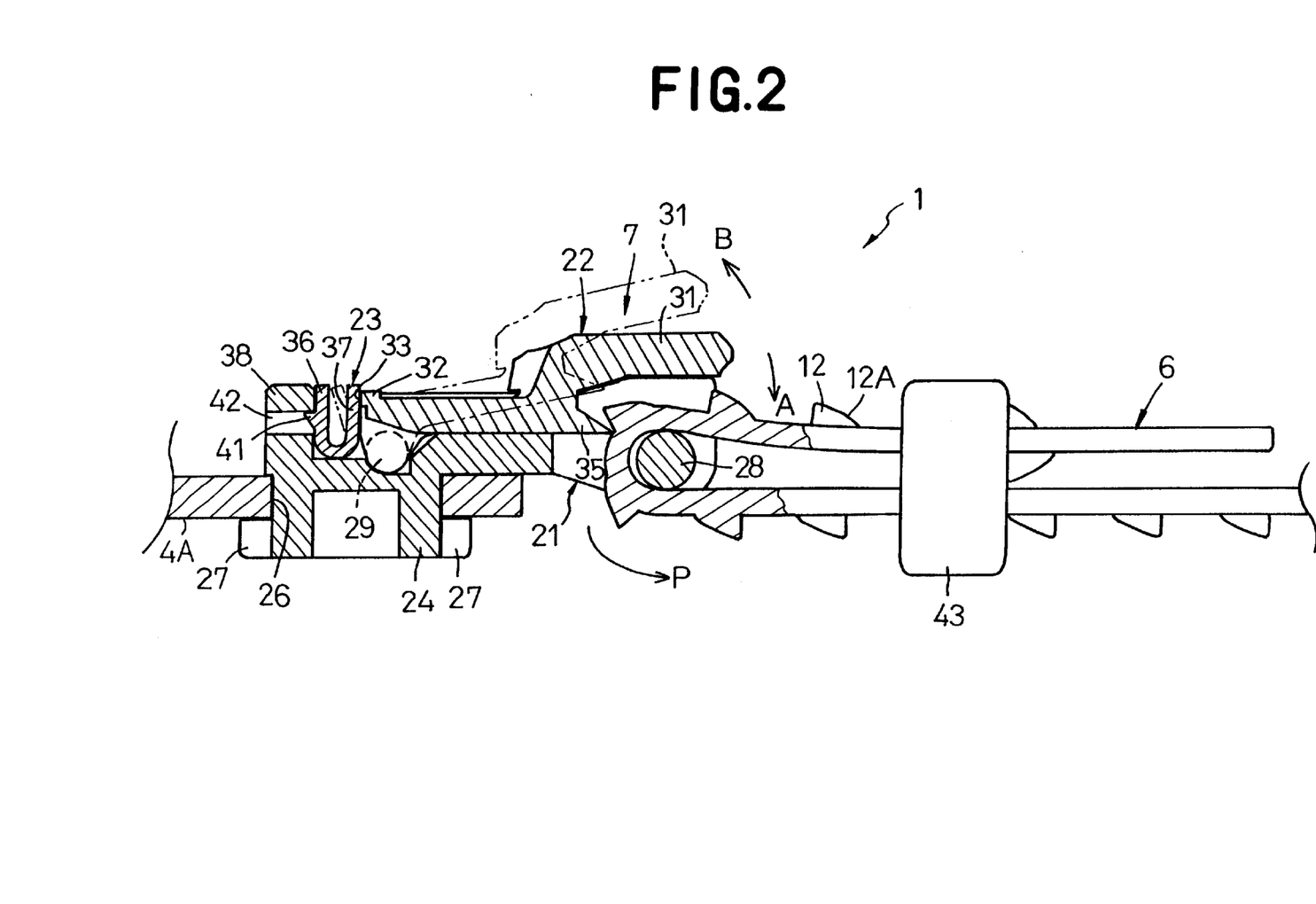
FIG. 2 is a sectional view taken along line II—II in FIG. 1.

FIG. 2 is a sectional view taken along line II—II in FIG. 1. The first support member 21 of the buckle 7 is coupled to the associated lateral end 4A of the frame 4 by means of a cylindrical portion 24 formed on the front end of the first support member 21 so that the first support member 21 may extend rearward from the lateral end 4A of the frame 4. The cylindrical portion 24 is inserted into a through-hole 26 of the lateral end 4A from its outer side so that a pair of stoppers 27 extending radially outward from a distal end of the cylindrical portion 24 may bear against the lateral end 4A of the frame 4 from its inner side and thereby the lateral end 4A of the frame 4 may be held between a proximal end of the cylindrical portion 24 and the pair of stoppers 27. In the vicinity of the rear end of the first support member 21, the head strap 6 is draped about a guide pin 28 extending transversely of the head strap 6.

Figure 3:
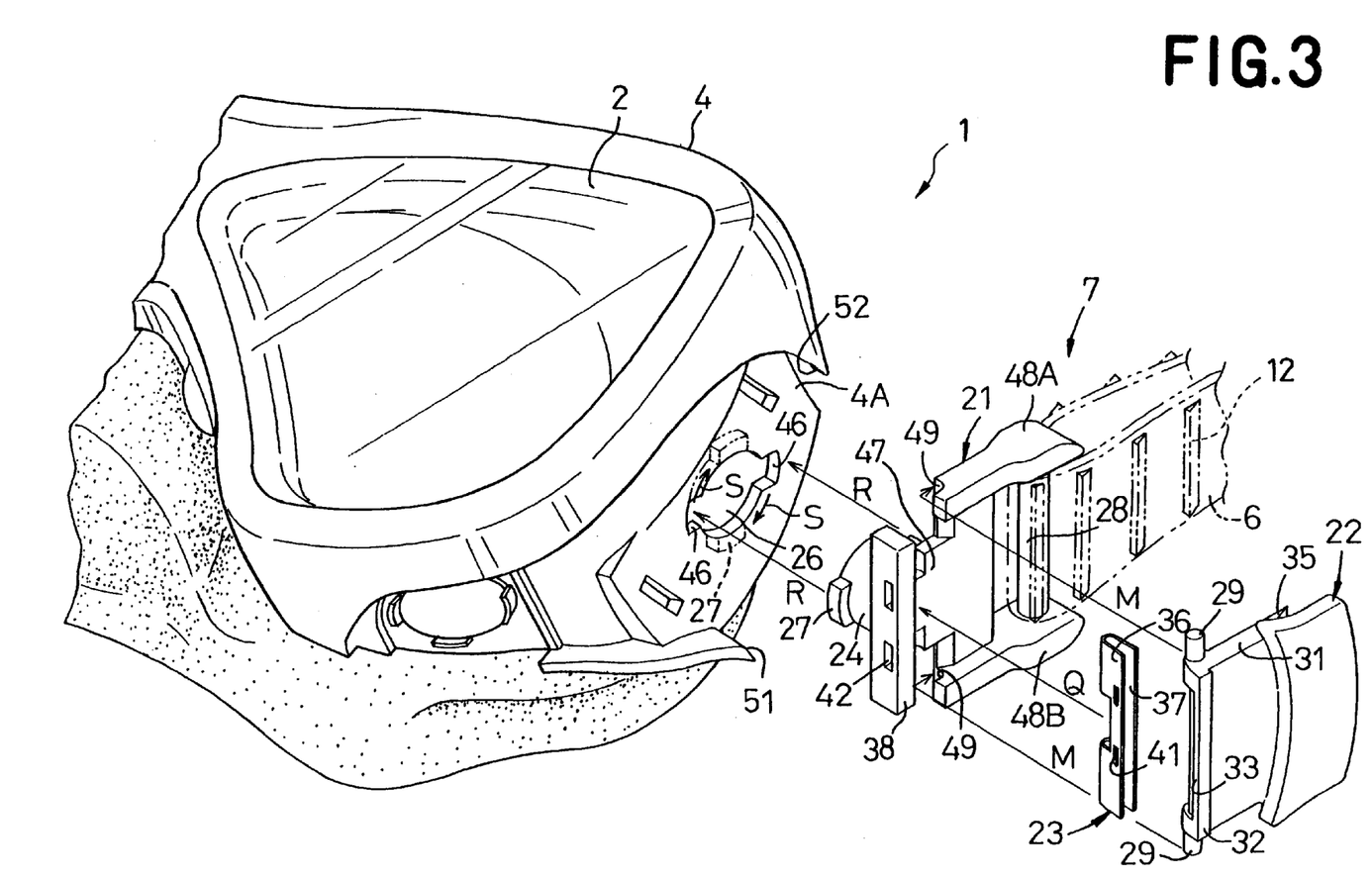
FIG. 3 is an exploded perspective view of a buckle.

The second support member 22 is pivotally supported by the first support member 21 around a pivot pin 29 (See FIGS. 1 and 3). A first arm 31 of the second support member 22 extending rearward from the pivot pin 29 can be swung around the pivot pin 29 either in a direction indicated by an arrow A or in a direction indicated by an arrow B with a mask wearer's finger placed on its distal end. The first arm 31 is formed on its inner surface with a second locking tooth 35 adapted to be engaged with one of the first locking teeth 12 of the head strap 6 as the first arm 31 is swung in the direction indicated by the arrow A, and thereby to prevent the head strap 6 from being slackened in a direction indicated by an arrow P. A second arm 32 of the second support member 22 extending forward from the pivot pin 29 has its distal end 33 pressed against of one side surface of the spring 23. In this manner, the spring 23 normally biases the second support member 22 to be swung in the direction indicated by the arrow A.

The spring 23 has a U-shaped cross-section defined by front and rear walls 36, 37 of this spring 23 and these front and rear walls 36, 37 are pressed against a wall 38 forming the distal end of the first support member 21 and the distal end 33 of the second support member 22, respectively, with the spring 23 being elastically deformed so as to reduce a width of its U-shape. Small projections 41 extending forward from the front wall 36 enter into openings 42 formed in the wall 38 of the first support member 21 and thereby prevents the spring 23 from slipping out upward as viewed in FIG. 2.

On the head strap 6, each of the first locking teeth 12 has an oblique rear surface 12A so that this rear surface 12A may cause the second support member 22 to swing in the direction indicated by the arrow B as the head strap 6 is pulled in the direction opposed to the direction indicated by the arrow P. Consequently, the second locking tooth 35 is moved upward away from the first locking tooth 12 and thereupon the head strap 6 can move so as to be tightened. It is also possible to swing the second support member 22 in the direction indicated by the arrow B with the mask wearer's finger placed upon the first arm 31. The second support member 22 swung in this manner and the spring 23 deformed by this second support member 22 are indicated by imaginary lines in FIG. 2.

FIG. 3 is an exploded perspective view showing the buckle 7 together with one of the lateral ends 4A of the lens frame 4 and the vicinity of this lateral end 4A. The through-hole 26 of the lateral end 4A is formed along its peripheral edge with a pair of diametrically opposite stopper guiding grooves 46. The first support member 21 of the buckle 7 comprises a flat plate-like portion 47 and a pair of side wall portions 48A, 48B integral with the plate-like portion 47 and extending rearward in parallel to each other. The plate-like portion 47 is formed on its forward end with a wall 38 and on its side facing the lateral end 4A of the frame 4 with the cylindrical portion 24. The guide pin 28 extends between the pair of side walls 48A, 48B and to guide the head strap 6 draped about it, as indicated by chain lines. The pair of side walls 48A, 48B are formed on their front portions with bearing portions 49 having circular-arc-shaped surfaces, respectively.

The second support member 22 of the buckle 7 includes a pair of pivot pins 29 extending vertically as viewed in FIG. 3 and these pivot pins 29 are slidably engaged with the respective bearing portions 49 of the first support member 21 in the direction indicated by an arrow M. The U-shaped spring 23 extends vertically as viewed in FIG. 3, i.e., transversely of the head strap 6 and preferably has a length corresponding to ½ or more of the second locking tooth 35 and more preferably substantially equal to the length of the second locking tooth 35. Such spring 23 is inserted between the wall 38 of the first support member 21 and the distal end 33 of the second support member 22 in the direction indicated by an arrow Q so that the spring 23 may be elastically deformed to reduce the width of said U-shape of the first support member 21 and the small projections 41 of the spring 23 may enter into the openings 42 as the pivot pin 29 comes in engagement with the bearing portions 49 (See FIG. 2). The spring 23 may be merely inserted between the first and second support members 21, 22 in the direction of the arrow Q laterally of the face mask after the first and second support members 21, 22 have been assembled. In this way, operation of assembling the buckle's components is extremely simplified. The spring 23 once inserted can be removed from the assembly by thrusting a fine rod into the respective openings 42 from the outer side to push the respective small projections 41 out of the respective openings 42.

The cylindrical portion 24 of the buckle 7 having been assembled in this manner is inserted into the through-hole 26 of the lens frame 4 as the stoppers 27 of the first support member 21 are aligned with the grooves 46 formed along the peripheral edge of the through-hole 26 and then said cylindrical portion 24 is rotated in a direction indicated by an arrow S until the stoppers 27 reach respective positions indicated by imaginary lines. This rotation is stopped when the lower side wall 48B of the first support member 21 bears against an overhang 51 extending outward from the lateral end 4A of the lens frame 4 (See FIG. 1 also). The buckle 7 is coupled to the lens frame 4 in this manner. In this buckle 7, the spring 23 lies between the first support member 21 and the second support member 22 as viewed in the back and forth direction of the face mask 1 and therefore a dimension (thickness) of the buckle 7 as measured diametrically of the front lenses is not affected by the presence of the spring 23. In other words, it is not apprehended that the buckles 7 might significantly project outward at temples of the mask wearer and increase a water-resistance of the face mask 1.

Along the section of the head strap 6 guided by each of the buckles 7, each of the first locking teeth 12 preferably has a length corresponding to ½ or more of the width of the strap 6, on one hand, and the second locking tooth 35 extending in parallel to the first locking teeth 12 preferably has a length equal to or larger than that of the first locking tooth 12, on the other hand. The spring 23 extending in parallel to the second locking tooth 35 has a length corresponding to ½ or more of the length of said second locking tooth 35. The face mask 1 comprising these first and second locking teeth 12, 35 and the spring 23 enables the spring 23 to act upon the head strap 6 over a wide area.

Figure 4:
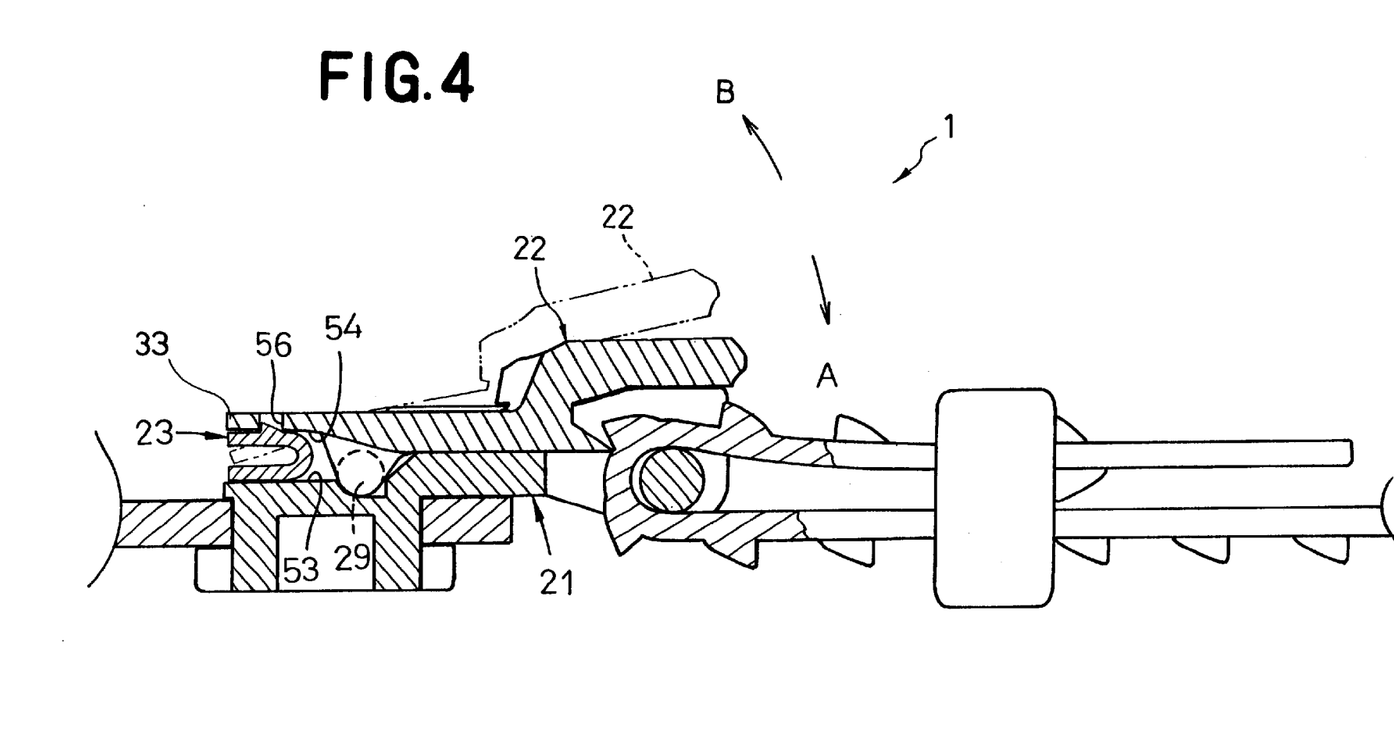
FIG. 4 is a view similar to FIG. 2 showing another embodiment of this invention.

FIG. 4 is a view similar to FIG. 2 showing another embodiment of this invention. In the buckle 7 of the face mask 1 according to this embodiment, the U-shaped spring 23 opening toward the lens frame 4 is disposed between the distal end of the first support member 21 lying immediately adjacent the face mask 1 and the distal end 33 of the second support member 22 lying outside and opposed to the first support member 21. More specifically, the U-shaped spring 23 is compressed between an outer surface 53 of the first support member 21 and an outer surface 54 of the second support member 22 so that a width of the U-shape may be reduced. The second support member 22 is normally biased by the spring 23 to swing in the direction indicated by the arrow A around the pivot pin 29. Also in the case of this face mask 1, the buckle 7 can be easily assembled merely by inserting the spring 23 from the front of the face mask 1 into the space between the first and second support members 21, 22 placed upon each other. Upon insertion of the spring 23 into the space, the small projection 41 enters into an opening 56 formed in the second support member 22 and prevents the spring 23 from slipping off out of the space between the first and second support members 21, 22.

Figure 5:
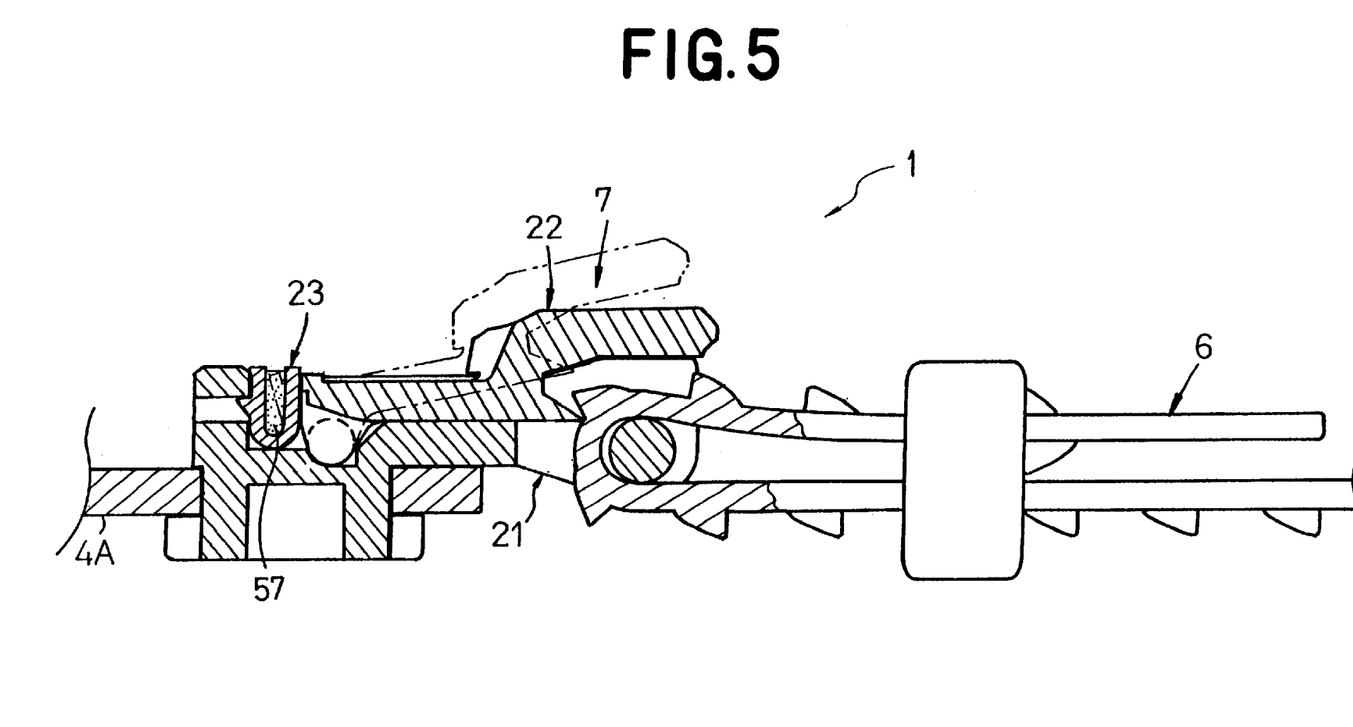
FIG. 5 is a view similar to FIG. 4 depicting yet another embodiment of this invention.

FIG. 5 is a view similar to FIG. 4 depicting another embodiment of this invention. The U-shaped spring 23 adopted by this face mask 1 is provided with an elastically compressible member 57 such as sponge filling a space defined inside the U-shape. The member 57 is effective to prevent the space from clogging with sand grains or the like.

Figure 6:
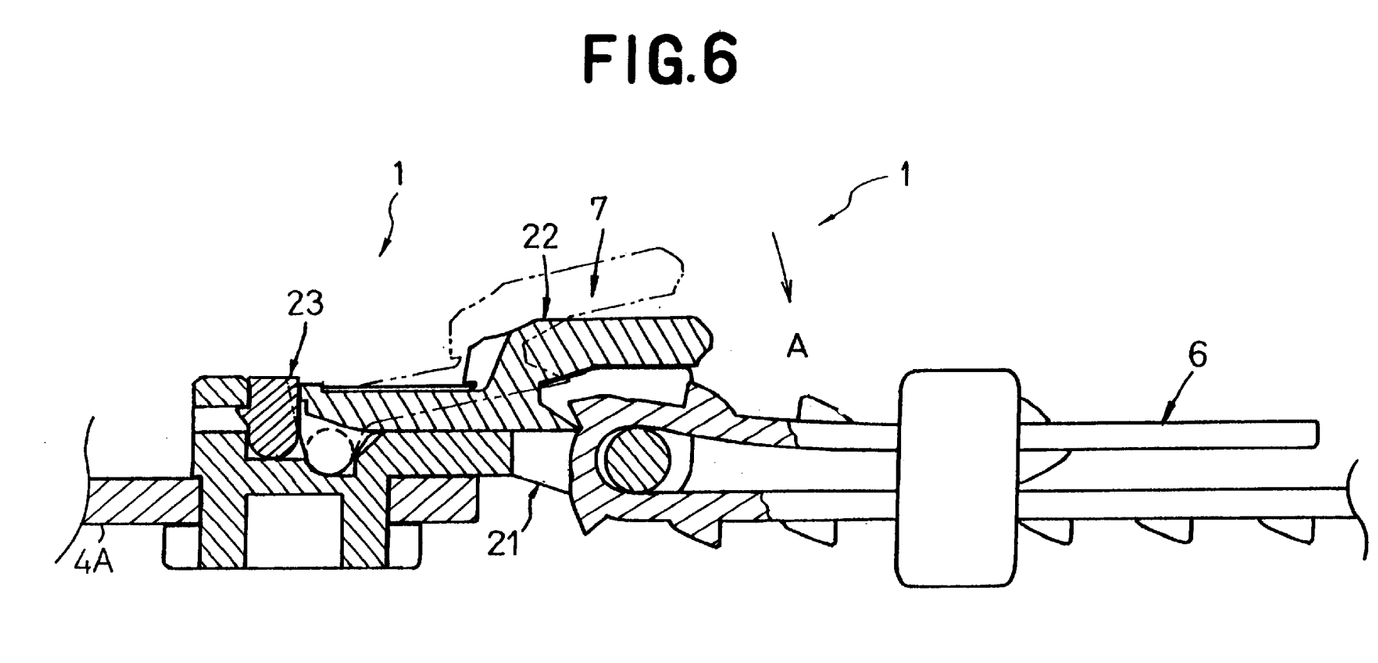
FIG. 6 is a view similar to FIG. 2 depicting still another embodiment of this invention.

FIG. 6 is a view similar to FIG. 2 depicting still another embodiment of this invention. In this specific embodiment of the face mask 1, the spring 23 comprises elastics such as rubber or plastic elastomer presenting a substantially rectangular cross-section and extending transversely of the head strap 6. The spring 23 is inserted between the first and second support members 21, 22 with its width elastically compressed in the horizontal direction as viewed in FIG. 6 and normally biases the second support member 22 to swing in the direction indicated by the arrow A. To facilitate the spring 23 to be inserted between the first and second support members 21, 22, the spring 23 is configured to have its lower end as viewed in FIG. 6 describing a circular arc.

While the first support member 21, is formed separately of the frame 4 as in the illustrated embodiments, it is possible without departing from the scope and the spirit of this invention to form the first support member 21 integrally with the frame 4. The first and second support members 21, 22 constituting the buckle 7 may be formed using rigid plastics and the spring 23 may be formed using rigid plastics, plastic elastomer or rubber. It is also possible to use any suitable metallic material to form the U-shaped spring 23. The face mask 1 according to this invention is useful not only for diving but also for skiing or motorbike riding.

What is claimed is:

1. A face mask comprising:
   a front lens;
   a skirt extending rearward from said front lens;
   a lens frame securing a front end of said skirt to a peripheral edge of said lens;
   a head strap; and
   buckles for length-adjustably coupling longitudinal opposite ends of said head strap to respective lateral ends of said lens frame,
   said head strap having a length direction, a width direction and a thickness direction orthogonal to said length and width direction, and
   each of said buckles comprising:
      a first support member and a second support member which cooperates with each other to hold said head strap therebetween, said first support member extending rearward from said lateral end of said lens frame and having a guide pin extending in said width direction of said head strap so that said head strap is folded back around said guide pin, said second support member being formed separately of said lens frame and pivotally supported by said first support member around a pivot pin, said second support member having a first arm extending rearward from said pivot pin and formed with a second locking tooth adapted to be selectively engaged with one of first locking teeth formed on a section of said head strap folded back around said guide pin; and
      a spring extending in said width direction of said head the spring being removable inserted into a space defined between a distal end of a second arm of said second support member extending forward from said pivot pin and a distal end of said first support member opposed to said distal end of said second support member so that said spring is compressed and elastically deformed between said distal ends to bias said second support member to swing until one of said first locking teeth comes in engagement with said second locking tooth thereby to prevent said head strap from moving in a slackening direction thereof.

2. The face mask according to claim 1, wherein said spring has a U-shaped cross-section and extends in said width direction of said head strap.

3. The face mask according to claim 2, wherein said spring is provided with an elastically compressible member filling a space defined inside the U-shape of said spring.

4. The face mask according to claim 1, wherein said spring has a rectangular cross-section and extends in said width direction of said head strap.

5. The face mask according to claim 1, wherein the distal end of said first support member is opposed to the distal end of said second support member as viewed alone a direction that extends between a back and a front of said face mask and said spring is inserted from a lateral side of said face mask into the space between said distal ends.

6. The face mask according to claim 1, wherein the distal end of said first support member is opposed to the distal end of said second support member as viewed along a direction that intersects a direction that extends between a back and a front of said face mask and said spring of said face mask is inserted from the front of said face mask into the space between said distal ends.

7. The face mask according to claim 1, wherein said spring has a length that is equal to at least one half of a length of said second locking tooth.

* * * * *

UNITED STATES PATENT AND TRADEMARK OFFICE
CERTIFICATE OF CORRECTION

PATENT NO.    : 6,350,030 B2
DATED         : December 19, 2002
INVENTOR(S)   : Taro Fujima

It is certified that error appears in the above-identified patent and that said Letters Patent is hereby corrected as shown below:

<u>Title page,</u>
Item [22], correct to read: -- Filed: Feb. 9, 2001 --

<u>Column 6,</u>
Line 49, change "alone" to -- along --.

Signed and Sealed this

Fourteenth Day of January, 2003

JAMES E. ROGAN
*Director of the United States Patent and Trademark Office*